US010163528B2

(12) United States Patent
Zhao et al.

(10) Patent No.: US 10,163,528 B2
(45) Date of Patent: Dec. 25, 2018

(54) DETERMINING USER-INTERESTED INFORMATION BASED ON WEARABLE DEVICE

(71) Applicant: Anhui Huami Information Technology Co., Ltd., Hefei, Anhui (CN)

(72) Inventors: Yajun Zhao, Anhui (CN); Jixiang Su, Hefei (CN); Fei Wang, Mountain View, CA (US); Ting Chen, Mountain View, CA (US); Hongda Mao, Mountain View, CA (US)

(73) Assignee: Anhui Huami Information Technology Co., Ltd., Hefei (CN)

( * ) Notice: Subject to any disclaimer, the term of this patent is extended or adjusted under 35 U.S.C. 154(b) by 38 days.

(21) Appl. No.: 15/584,911

(22) Filed: May 2, 2017

(65) Prior Publication Data

US 2017/0242974 A1 Aug. 24, 2017

Related U.S. Application Data

(63) Continuation-in-part of application No. PCT/CN2016/105720, filed on Nov. 14, 2016.

(30) Foreign Application Priority Data

Nov. 17, 2015 (CN) .......................... 2015 1 0795936
Nov. 17, 2015 (CN) .......................... 2015 1 0796544

(51) Int. Cl.
*A61B 5/04* (2006.01)
*G16H 50/30* (2018.01)
(Continued)

(52) U.S. Cl.
CPC ........... *G16H 50/30* (2018.01); *A61B 5/0245* (2013.01); *A61B 5/02438* (2013.01);
(Continued)

(58) Field of Classification Search
CPC .............. A61B 5/02438; A61B 5/0245; A61B 5/04023; A61B 5/0452; A61B 5/726;
(Continued)

(56) References Cited

U.S. PATENT DOCUMENTS 8,897,863 B2 * 11/2014 Linker ............... A61B 5/04012
600/508
2009/0070266 A1 * 3/2009 Shah .................... A61B 5/0002
705/51

(Continued)

FOREIGN PATENT DOCUMENTS

CN 101773394 A 7/2010
CN 103038772 A 4/2013
(Continued)

OTHER PUBLICATIONS

Wang, Ruxiang, "Research on Algorithms of Automatic Detection for Arrhythmia." China Master's Theses Full-text database (2013, issue 11, 136-57).

*Primary Examiner* — George Manuel
(74) *Attorney, Agent, or Firm* — Young Basile Hanlon & MacFarlane, P.C.

(57) ABSTRACT

This disclosure provides wearable-device based user-interested information determination methods, apparatuses and wearable devices. The method includes: receiving, by an electrocardiography (ECG) sensor associated with the wearable device, an ECG signal of a user, determining a feature set for the ECG signal, in which the feature set includes time-domain feature data of the ECG signal and frequency-domain feature data of the ECG signal, and determining the user-interested information based on similarity between the feature set and reference feature sets indicative of the user-interested information, in which the user-interested information includes health information associated with a disease. The wearable device includes an ECG sensor con- (Continued)

figured to receive an ECG signal and an FPGA system. The FPGA system includes modules for determine user-interested information based on the ECG signal. The apparatus includes a processor and a memory coupled to the processor. The memory is configured to store instructions to implement the method.

16 Claims, 16 Drawing Sheets

(51) Int. Cl.
  *A61B 5/0452* (2006.01)
  *G06F 21/32* (2013.01)
  *G16H 40/63* (2018.01)
  *A61B 5/024* (2006.01)
  *A61B 5/0245* (2006.01)
  *A61B 5/0402* (2006.01)
  *A61B 5/00* (2006.01)
  *G06F 17/14* (2006.01)
  *G06F 17/15* (2006.01)
  *G06F 19/00* (2018.01)
  *G06F 17/50* (2006.01)

(52) U.S. Cl.
  CPC ........ *A61B 5/04023* (2013.01); *A61B 5/0452* (2013.01); *A61B 5/726* (2013.01); *A61B 5/7282* (2013.01); *G06F 17/147* (2013.01); *G06F 17/148* (2013.01); *G06F 17/15* (2013.01); *G06F 19/00* (2013.01); *G06F 21/32* (2013.01); *G16H 40/63* (2018.01); *G06F 17/5027* (2013.01)

(58) Field of Classification Search
  CPC ... A61B 5/7282; G06F 17/147; G06F 17/148; G06F 17/15; G06F 17/5027; G06F 19/00; G06F 21/32; G16H 40/63; G16H 50/30
  See application file for complete search history.

(56) References Cited

U.S. PATENT DOCUMENTS

| | | |
|---|---|---|
| 2010/0274100 A1 | 10/2010 | Behar et al. |
| 2013/0184517 A1 | 7/2013 | Collier |
| 2015/0164349 A1 | 6/2015 | Gopalakrishnan et al. |
| 2015/0164410 A1 | 6/2015 | Selvaraj et al. |

FOREIGN PATENT DOCUMENTS

| | | | |
|---|---|---|---|
| CN | 103093133 | A | 5/2013 |
| CN | 103584852 | A | 2/2014 |
| CN | 103610457 | A | 3/2014 |
| CN | 104055499 | A | 9/2014 |
| CN | 104382584 | A | 3/2015 |
| CN | 104382590 | A | 3/2015 |
| CN | 104510463 | A | 4/2015 |
| CN | 104573458 | A | 4/2015 |
| CN | 104720846 | A | 6/2015 |
| CN | 105286853 | A | 2/2016 |
| CN | 105468951 | A | 4/2016 |
| WO | 2010135516 | A2 | 11/2010 |

\* cited by examiner

DETERMINING USER-INTERESTED INFORMATION BASED ON WEARABLE DEVICE

CROSS-REFERENCE TO RELATED APPLICATION(S)

This application is a continuation-in-part of International Application No. PCT/CN2016/105720, filed on Nov. 14, 2016, which claims priority to both Chinese Patent Application No. 201510795936.2, filed on Nov. 17, 2015 and Chinese Patent Application No. 201510796544.8, filed on Nov. 17, 2015, the contents of all of which are hereby incorporated by reference in their entireties.

BACKGROUND

With development of society, improvement of living standards, and rapid development of mobile internet, wearable devices with its wearable convenience entered into people's daily lives.

SUMMARY

Disclosed herein are implementations of method, apparatus and wearable devices for determining user-interested information based on a wearable device.

In one aspect, a method for determining user-interested information based on a wearable device is provided. The method includes: receiving, by an electrocardiography (ECG) sensor associated with the wearable device, an ECG signal of a user, determining a feature set for the ECG signal, wherein the feature set comprises time-domain feature data of the ECG signal and frequency-domain feature data of the ECG signal, and determining the user-interested information based on similarity between the feature set and reference feature sets indicative of the user-interested information, wherein the user-interested information comprises health information associated with a disease.

In another aspect, a wearable apparatus is provided in this disclosure, which includes: an electrocardiography (ECG) sensor, configured to receive an ECG signal of a user, and a field-programmable gate array (FPGA) system, configured to determine user-interested information based on the ECG signal. The FPGA system further includes: a feature set determination module, configured to determine a feature set for the ECG signal, wherein the feature set comprises time-domain feature data of the ECG signal and frequency-domain feature data of the ECG signal, and a result determination module, configured to determine the user-interested information based on similarity between the feature set and reference feature sets indicative of the user-interested information, wherein the user-interested information comprises at least one of health information associated with a disease and identity information associated with an identity.

In another aspect, an apparatus for determining user-interested information based on a wearable device is provided in this disclosure, which includes a processor and a memory coupled to the processor. The memory is configured to store a set of instructions which when executed by the processor become operational with the processor to: receive, by an electrocardiography (ECG) sensor associated with the wearable device, an ECG signal of a user, determine a feature set for the ECG signal, wherein the feature set comprises time-domain feature data of the ECG signal and frequency-domain feature data of the ECG signal, and determining the user-interested information based on similarity between the feature set and reference feature sets indicative of the user-interested information, wherein the user-interested information comprises health information associated with a disease.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
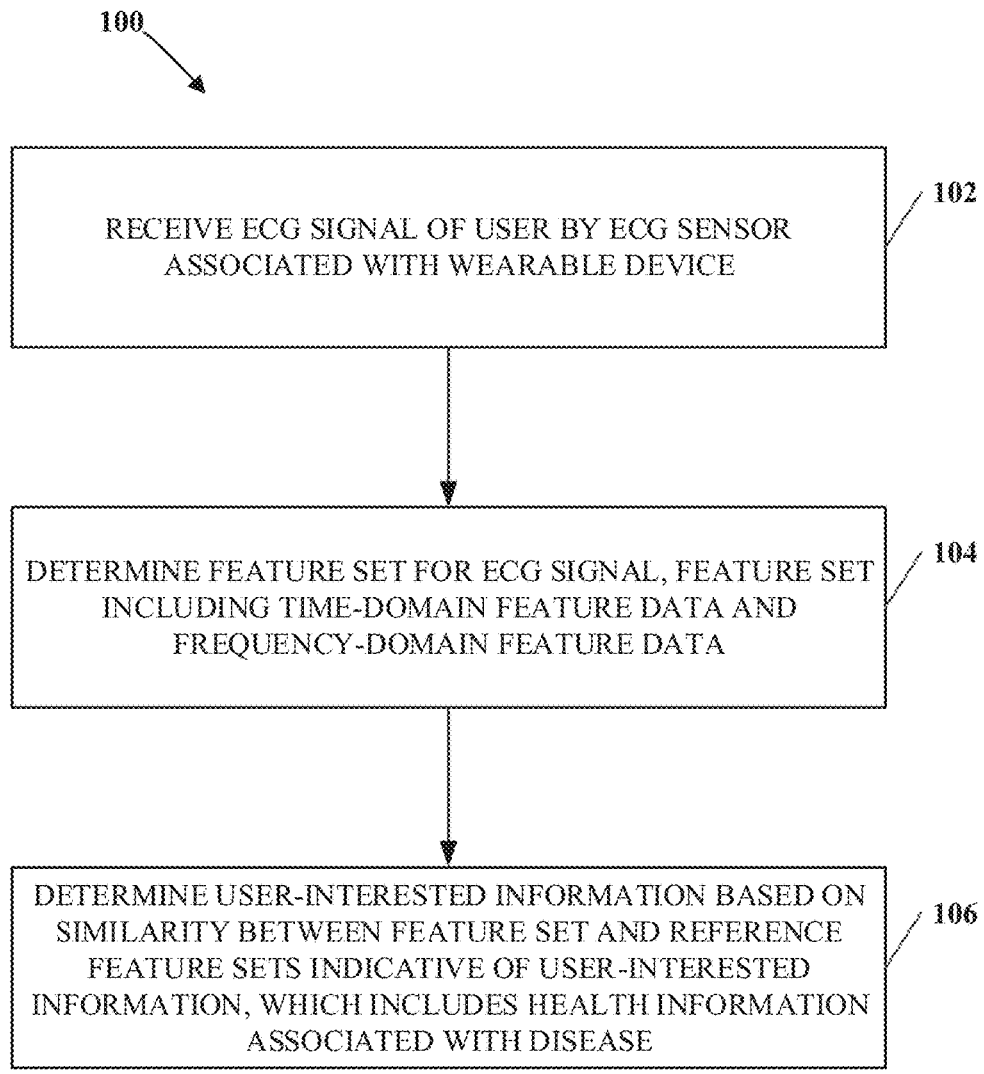
FIG. 1 is a flowchart of an example process for determining user-interested information based on a wearable device according to an implementation of this disclosure.

FIG. 1 is a flowchart of an example process 100 for determining user-interested information based on a wearable device according to an implementation of this disclosure. As shown in FIG. 1, the process can include the following operations.

At operation 102, an original electrocardiography (ECG) signal (or simply referred to as an "ECG signal" hereinafter) of a user is received by an ECG sensor associated with a wearable device.

At operation 104, a feature set of the original ECG signal is determined. The feature set can include time-domain feature data of the original ECG signal and frequency-domain feature data of the original ECG signal. For example, the feature set can include a feature vector (e.g., an eigenvector) of the original ECG signal.

At operation 106, user-interested information is determined based on similarity between the feature set of the original ECG signal and reference feature sets representing the user-interested information. For ease of explanation, a feature set is referred to as a "feature vector" hereinafter.

In an implementation, the user-interested information can include health information. For example, the health information can indicate whether the user is having a disease (e.g., a cardiovascular disease). The user-interested information can also include identity information. For example, the identity information can indicate whether the user is authorized.

Implementations of this disclosure can be described using the following examples. Compared with fingerprints, face images, iris, and other biological features, an ECG signal of a human body is determined by heart structures of an individual, and can have features such as being universal, unique, easy to collect, or permanent. Moreover, ECG signals have advantages, such as only existing in a living body, not easy to be imitated, or not easy to lose. By collecting ECG signals using wearable devices and detecting cardiovascular diseases, users can timely detect abnormalities in the body and receive medical treatment in time.

In an implementation of this disclosure, an original ECG signal of a user can be received by an ECG sensor integrated in a wearable device. A feature vector (e.g., a feature vector) of the original ECG signal can be determined. A disease (e.g., a disease type) associated with the original ECG signal can be determined or detected based on similarity between the feature vector of the original ECG signal and a reference feature vector associated with an ECG signal that can be used to identify or indicate a disease (referred to as a "disease ECG signal"). The feature vector can include time-domain feature data and frequency-domain feature data of the original ECG signal. By detecting diseases for the user based on the feature vector of the ECG signal, accuracy of disease detection for the user can be improved, and early detection of diseases can be realized using wearable devices.

Figure 2A:
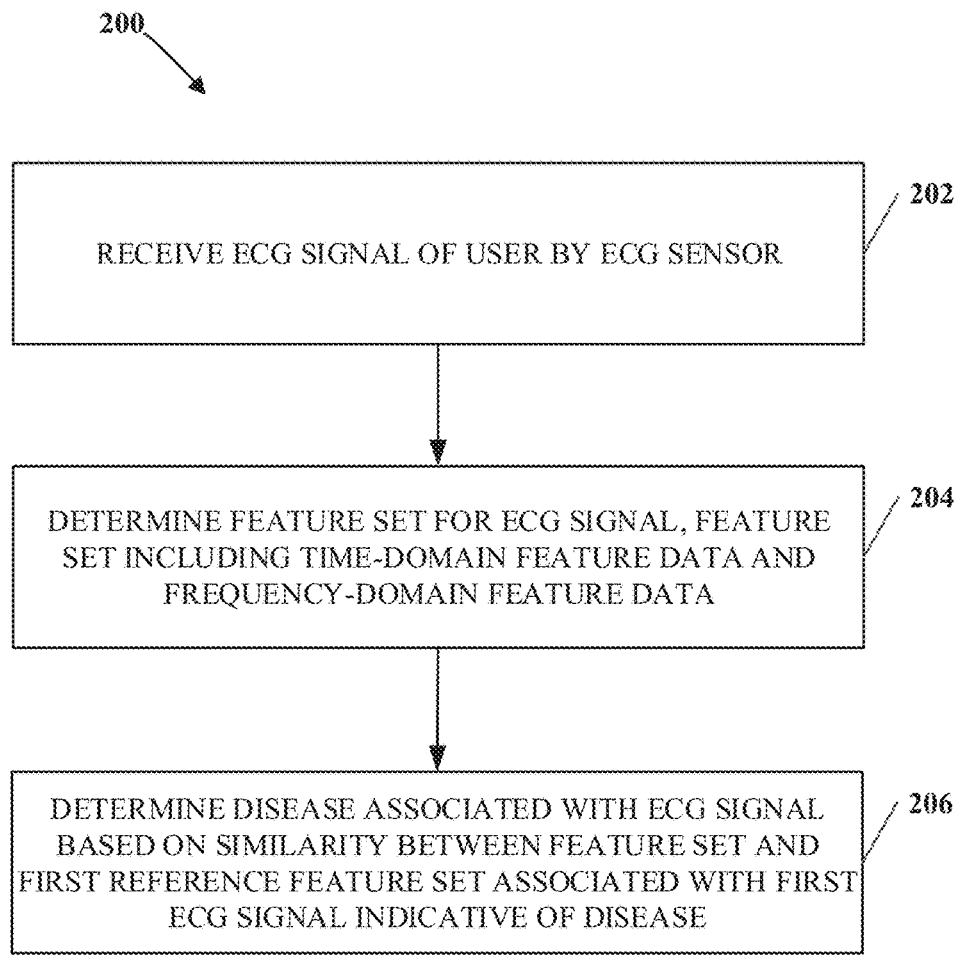
FIG. 2A is a flowchart of an example process for disease detection based on a wearable device according to an implementation of this disclosure.
Figure 2B:
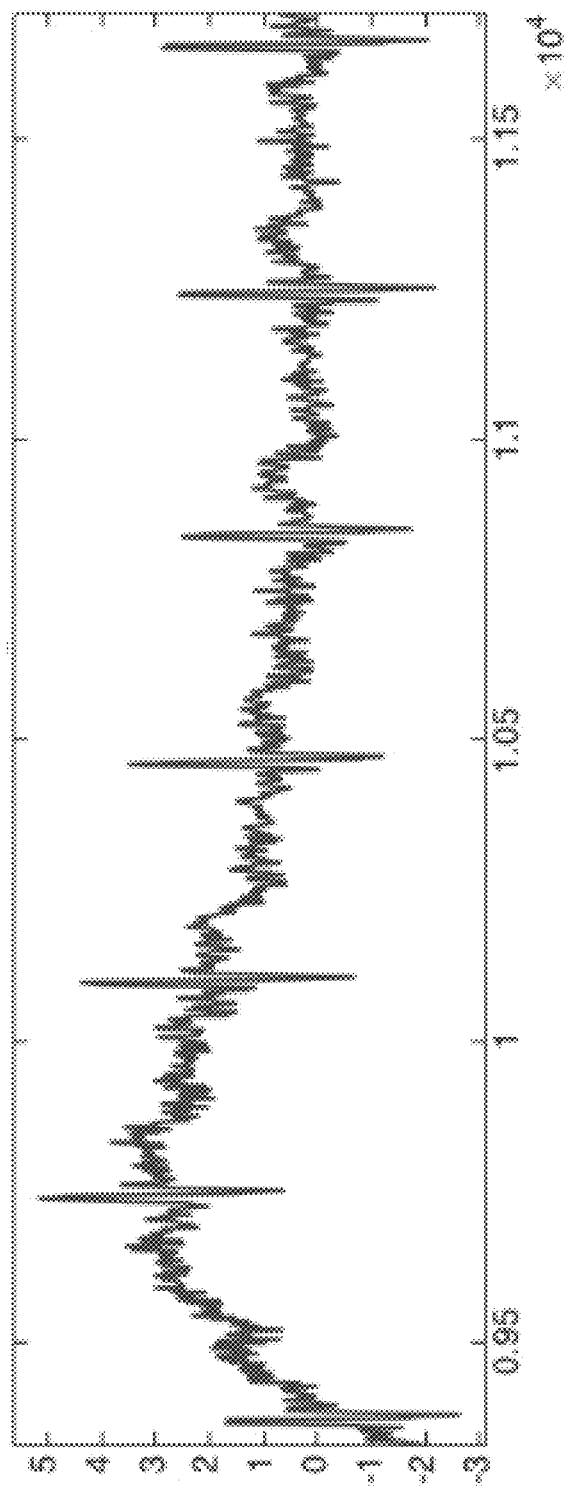
FIG. 2B is a diagram of an original ECG signal.

Examples are provided as follows to describe implementations of this disclosure. FIG. 2A is a flowchart of an example process 200 for disease detection based on a wearable device according to an implementation of this disclosure. FIG. 2B is a diagram of an original ECG signal. In an implementation, a disease detection method based on a wearable device can be used at the wearable device. In an example, the wearable device can be a smart wristband. The wearable device can include an ECG sensor. Referring to FIG. 2A, the disease detection method can include the following operations.

At operation 202, an original ECG signal of a user is received by an ECG sensor.

At operation 204, a feature vector (e.g., a feature vector) of the original ECG signal is determined. The feature vector can include time-domain feature data of the original ECG signal and frequency-domain feature data of the original ECG signal.

At operation 206, a disease (e.g., a disease type) associated with the original ECG signal is determined based on similarity between the feature vector of the original ECG signal and reference feature vectors of disease ECG signals that are indicative of different diseases.

At the operation 202, as shown in FIG. 2B, the ECG signal received by the ECG sensor can include noise, and the noise can vary over time. However, ECG signals of the same user received at different times can have similar features, such as, for example, QRS wave groups, P waves, and T waves.

At the operation 204, in an implementation, the frequency-domain feature data of the original ECG signal can include wavelet coefficients associated with the original ECG signal determined from a wavelet transform, discrete cosine transform (DCT) coefficients determined from a DCT transform, Fourier transform coefficients determined from a Fourier transform, Hilbert-Hwang Transform (HHT) coefficients determined from an HHT transform, or any other transform coefficients determined from any transform performed on the ECG signal. This disclosure is not limited to use any specific conversion or transformation.

At the operation 206, in some implementations, ECG data of the users can be used to obtain reference feature vectors (e.g., reference feature vectors) for the disease ECG signals using a training technique. In an implementation, reference feature vectors (e.g., eigenvectors) of the disease ECG signals can be determined from an offline training technique, and, when detecting the disease, the reference feature vectors obtained from training the ECG signals can be used. The similarity between the feature vector of the original ECG signal and reference feature vectors of disease ECG signals can be determined using a nearest neighbor method that comprises a matrix model. For example, the matrix model used in the nearest neighbor method can be obtained from a machine learning technique. The goal of the machine learning technique is to improve the accuracy of the similarity determination to ensure the accuracy of the disease detection.

As described above, in an implantation, an original ECG signal of a user can be received by an ECG sensor. A feature vector (e.g., a feature vector) of the original ECG signal can be determined. A similarity determination technique (e.g., the nearest neighbors method) can be used to determine the similarity between the feature vector of the original ECG signal and a reference feature vectors associated with disease ECG signals that can be used to identify or indicate various diseases. Based on the similarity, a disease (e.g., a disease type) can be determined for the original ECG signal. Because the feature vector can include time-domain feature data and frequency-domain feature data of the original ECG signal, and a matrix model can be used in the similarity determination technique and obtained from a machine learning technique, accuracy of disease detection for the user can be increased.

Figure 3A:
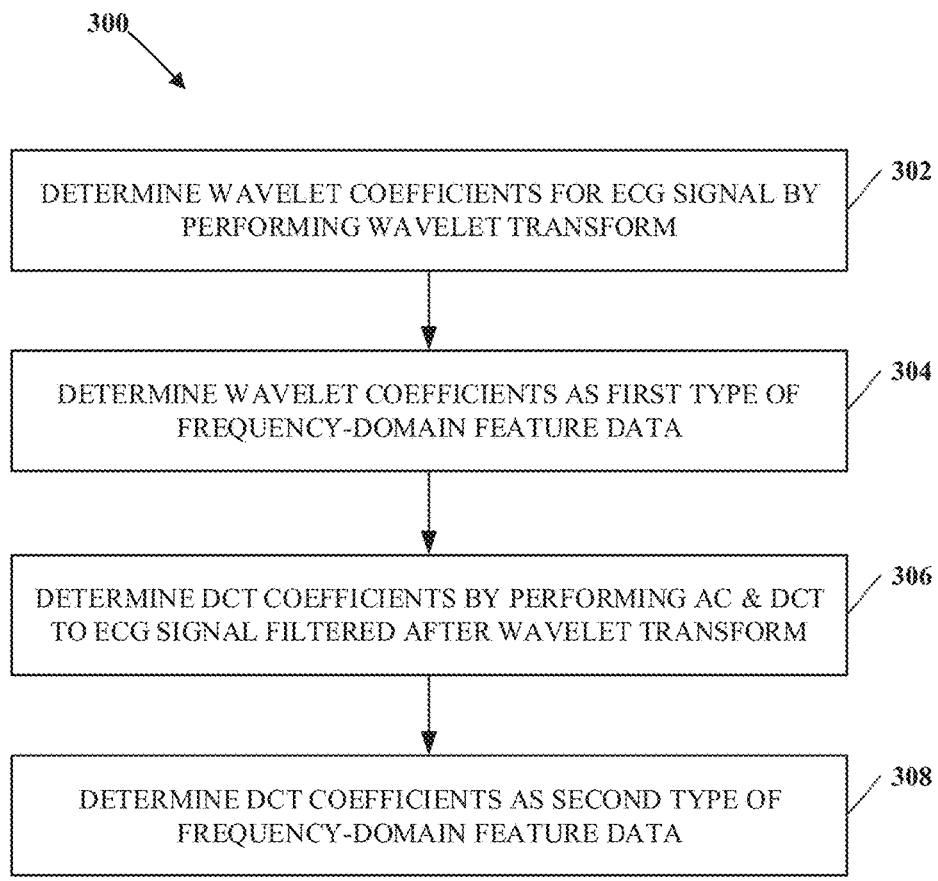
FIG. 3A is a flowchart of an example process for determining frequency-domain feature data of an original ECG signal according to an implementation of this disclosure.
Figure 3B:
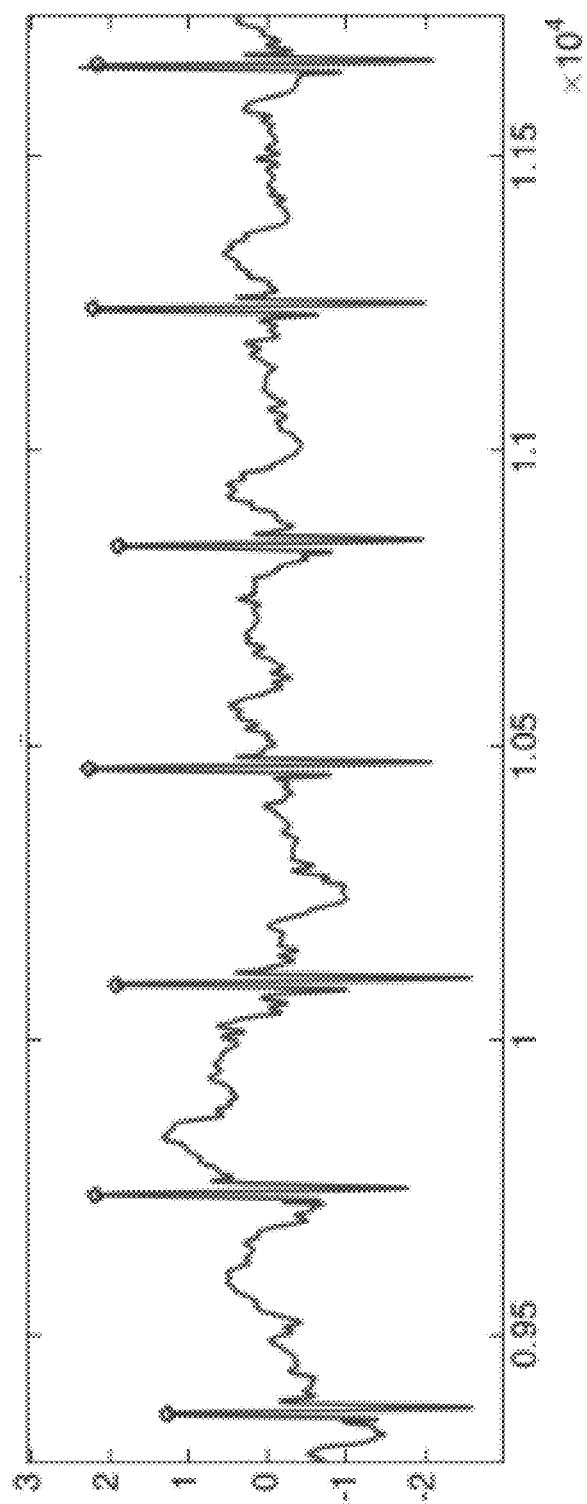
FIG. 3B is a diagram of an ECG signal after noise reduction by performing a wavelet transform according to an implementation of this disclosure.

FIG. 3A is a flowchart of an example process 300 for determining frequency-domain feature data of an original ECG signal according to an implementation of this disclosure. FIG. 3B is a diagram of an ECG signal after noise reduction by performing a wavelet transform according to an implementation of this disclosure. As shown in FIG. 3A, the frequency-domain feature data of the original ECG signal can be determined using the following operations.

At operation 302, a wavelet transform is performed to the original ECG signal to obtain wavelet coefficients for the original ECG signal.

At operation 304, the wavelet coefficients are determined as a first type of the frequency-domain feature data of the original ECG signal.

At operation 306, autocorrelation (AC) and DCT are performed to the ECG signal after the wavelet transform to obtain DCT coefficients after the AC and DCT.

At operation 308, the DCT coefficients are determined as a second type of the frequency-domain feature data of the original ECG signal.

At the operation 302, the wavelet transform can decompose signals of different frequencies from the original ECG signal. As high-frequency noise of the original ECG signal is mainly represented in low scales, and low-frequency noise of the original ECG signal is mainly represented at high scales, by analyzing the original ECG signal using intermediate scales after the wavelet transform, effective signals can be separated from interference noise signals. In an implementation, the original ECG signals can be decomposed by the wavelet transform to obtain wavelet coefficients associated with the original ECG signals. For example, the wavelet transform can apply groups of high-pass and low-pass filters with predetermined coefficients to the original ECG signal. The wavelet coefficients can be at multiple scales. In another implementation, the wavelet transform for the original ECG signals can be performed in forms of bitwise operations (e.g., shifting) and addition operations. The shifting and addition operations can be performed on a hardware platform. The hardware platform can be, for example, a field-programmable gate array (FPGA) system. The logic of the shifting and addition operations can be simple and easy to implement. As shown in FIG. 3B, after the wavelet transform, the noise in the original ECG signal can be effectively reduced, causing the ECG signal to become more regular.

At operation 306, in an implementation, AC can be performed to the filtered ECG signal to reduce irrelevant portions for detection or recognition from the ECG signal. After the AC operation, DCT can be further performed to the ECG signal to obtain DCT coefficients. In another implementation, Fourier transform or HHT can be performed to the filtered ECG signal, and Fourier transform coefficients or HHT coefficients obtained therefrom can be used as a third type of the frequency-domain feature data of the ECG signal.

In this implementation, the noise of the original ECG signal can be filtered by the wavelet transform, causing the ECG signal to be more regular. The wavelet coefficients and the DCT coefficients of the original ECG signal at various scales can more accurately represent features of the original ECG signal in the frequency domain.

Figure 4A:
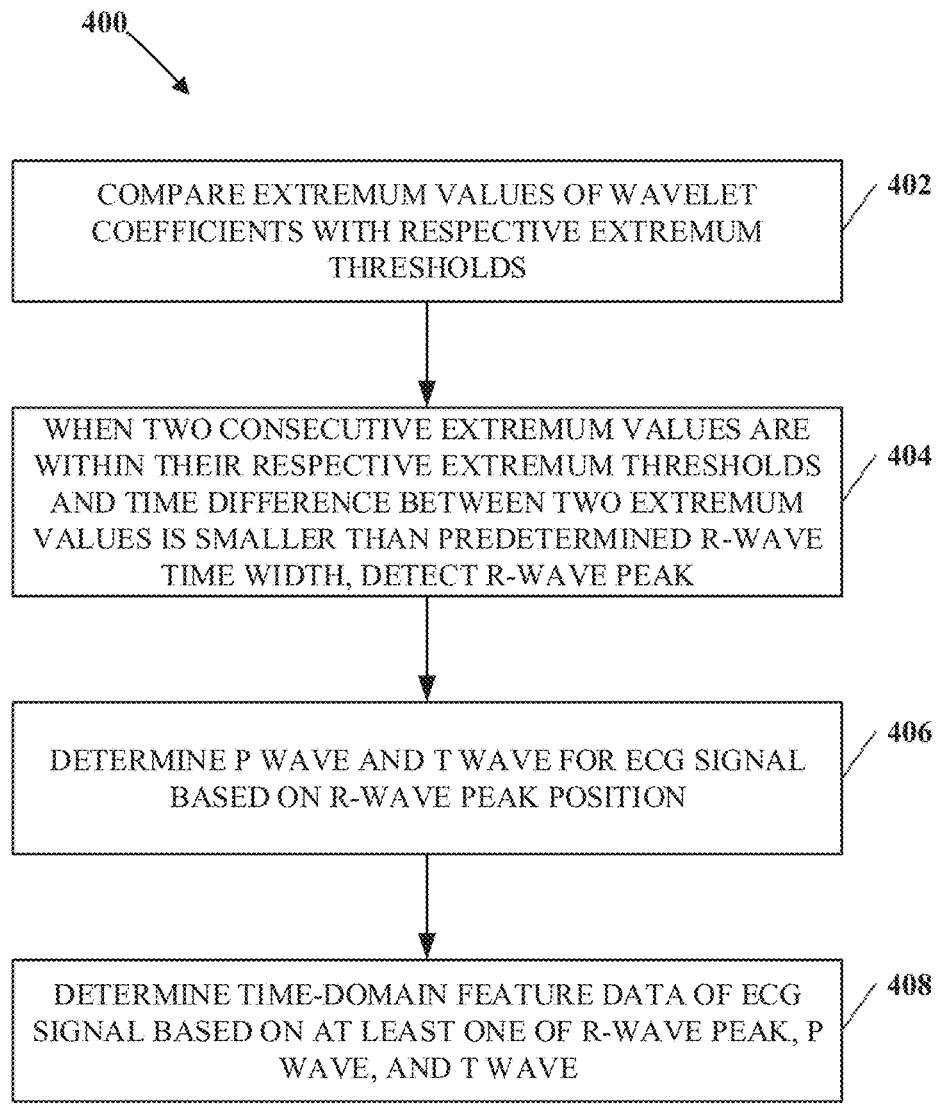
FIG. 4A is a flowchart of an example process for determining time-domain feature data of an original ECG signal according to an implementation of this disclosure.
Figure 4B:
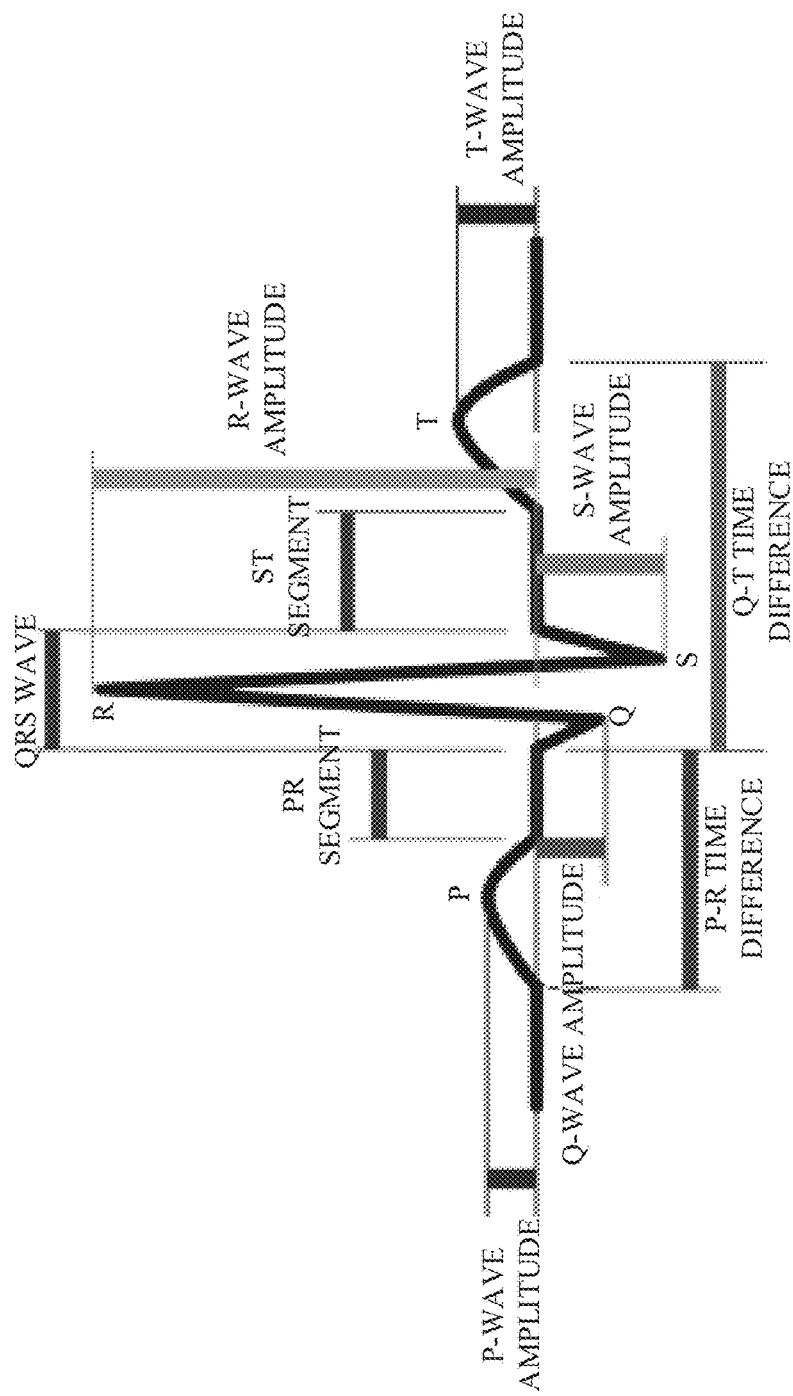
FIG. 4B is a diagram of example temporal and amplitude feature data of an ECG signal.
Figure 4C:
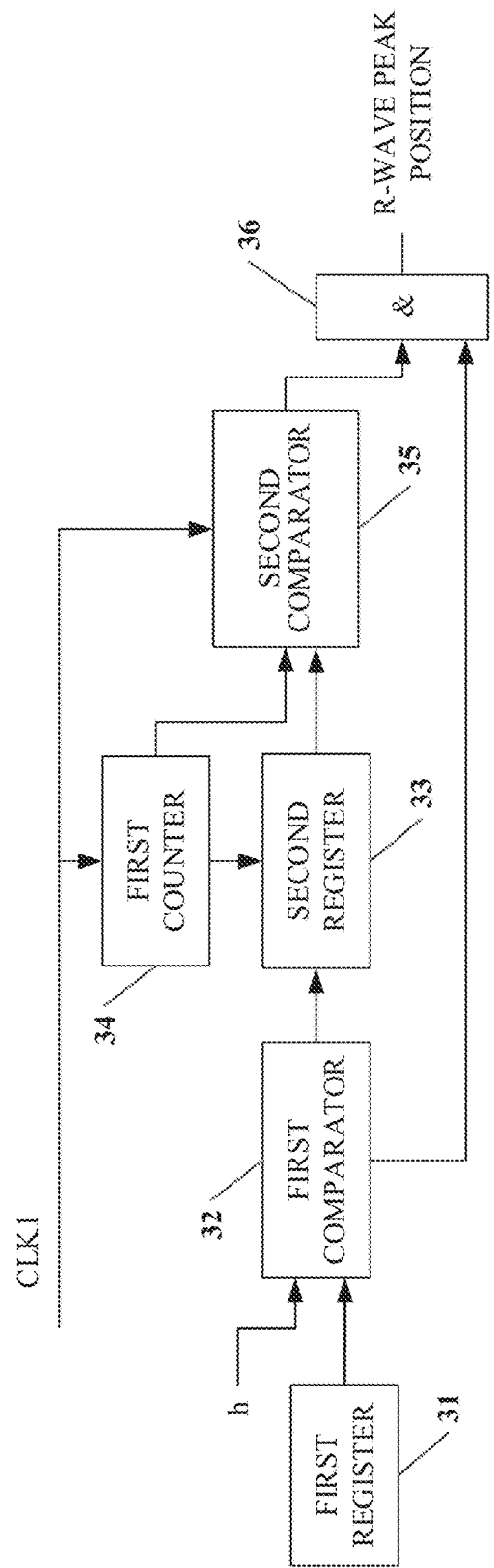
FIG. 4C is a diagram of an example hardware circuit for detecting R-wave peaks.
Figure 4D:
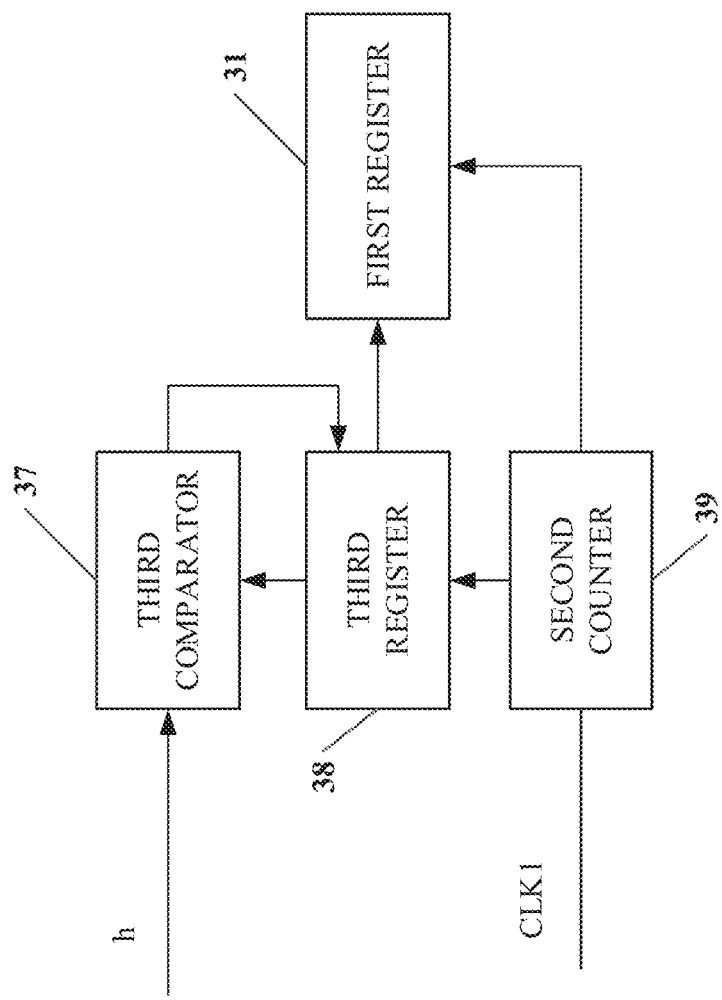
FIG. 4D is a diagram of an example circuit for detecting a dynamic threshold.

FIG. 4A is a flowchart of an example process 400 for determining time-domain feature data of an original ECG signal according to an implementation of this disclosure. FIG. 4B is a diagram of example temporal and amplitude feature data of an ECG signal. FIG. 4C is a diagram of an example hardware circuit for detecting R-wave peaks. FIG. 4D is a diagram of an example circuit for detecting a dynamic threshold. As illustrated in FIG. 4A, the time-domain feature data of the original ECG signal can be determined using the following operations.

At operation 402, extremum values of the wavelet coefficients are compared with (e.g., by a comparator) respective extremum thresholds. The extremum values can include maximum values, minimum values, or a combination thereof. For each of the extremum values, there can be a corresponding extremum value threshold. For example, it can be determined whether a first extremum value is within a first extremum value threshold and a second extremum value is within a second extremum value threshold.

At operation 404, detection of the R-wave peak (a peak of an R wave) is triggered when two consecutive extremum values are within their respective extremum thresholds and a time difference between the two extremum values is smaller than a predetermined R-wave time width. For example, if the first extremum value and the second extremum value are consecutive, the R-wave peak can be determined when the first extremum value is within the first extremum value threshold, the second extremum value is within the second extremum value threshold, and a time difference between the first extremum value and the second extremum value is smaller than the predetermined R-wave time width.

At operation 406, a P wave and a T wave of the ECG signal are determined or extracted based on a position of the R-wave peak (or, a peak position of the R wave).

At operation 408, the time-domain feature data of the ECG signal is determined from at least one of the R-wave peak, the P wave, and the T wave.

As shown in FIG. 4B, the time-domain feature data of the ECG signal can include at least one of: the peak position of the R wave, a peak position of the P wave, a peak position of the T wave, an amplitude of the P wave, an amplitude of the R wave, an amplitude of the T wave, a difference between the peak position of the P wave and the peak position of the R wave, a difference between the peak position of the T wave and the position of the peak position of the R wave, a PR segment, and an ST segment.

In FIG. 4B, in an implementation, the wavelet transform is performed to the original ECG signal. For example, the wavelet transform can include a quadratic-spline discrete wavelet transform. If singularity of the original ECG signal is an intersection of a rising edge and a falling edge, after the wavelet transform, a signal associated with the intersection can become a zero-crossing point between a minimum value and a maximum value (referred to as an "extremum value pair"). The zero-crossing point of the extreme value pair is an onset position of the R wave of the ECG signal. Therefore, the R-wave peak position can be detected using the zero-crossing point of the extreme value pair of the original ECG signal after the wavelet transform being applied. The P wave and the T wave can be determined using a similar method. Example time-domain feature data of an ECG signal is shown in FIG. 4B.

In an implementation, the P wave and the T wave can be determined or detected using a previously detected R wave. For example, after the R-wave peak being determined, a P wave can be detected before the R-wave peak. For example, the P wave can be searched in a time interval from 250 microsecond (ms) before the R-wave peak to 150 ms before the R-wave peak. For another example, the T wave can be detected after the R-wave peak. For example, a T wave can be searched in a time interval from 170 ms after the R-wave peak to 400 ms after the R-wave peak.

In another implementation, the PQRST wave is continuous. Based on the R-wave peak, a Q wave can be detected forwardly and an S wave can be detected backwardly. A P wave can be detected based on the Q wave, and a T wave can be detected based on the S wave. In this implementation, detection speed can be increased, and detection error rate can be reduced.

In another implementation, feature data of the Q wave and the S wave in time domain can also be used as the time-domain feature data, so that the feature representation of the ECG signal in the time domain can be further improved.

In an implementation, a hardware circuit can be used for detection of the time-domain feature data of the ECG signal. As shown in FIG. 4C, the R-wave peak position can be detected by an example hardware circuit.

In an implementation, a first comparator 32 can compare the extremum value h in the wavelet coefficients with an extremum value threshold stored in a first register 31. For example, for the first comparison, a default value stored in a second register 33 can be zero.

For example, when the first comparator 32 determines that a maximum value is smaller than an upper threshold in the first register 31, the first comparator 32 can send a first logic signal 1 to an AND gate 36. The first comparator 32 can also provide a second logic signal to a second register 33. Based on the second logic signal, the second register 33 can send the default value 0 to a second comparator 35. The second register 33 can further store a first count from a first counter 34, in which the first count can be associated with a time corresponding to the maximum value. The first counter 34 can send the time corresponding to the maximum value to the second comparator 35. The second comparator 35 can calculate a difference between the time corresponding to the maximum value and 0, and then further compare the difference with a predetermined R-wave time width. The predetermined R-wave time width can include a theoretical value (e.g., 0.1 s). When the second comparator 35 determines that the difference is greater than the predetermined R-wave time width, it can send a third logic signal 0 to the AND gate 36. When the AND gate 36 receives the first logic signal 1 from the first comparator 32 and the third logic signal 0 from the second comparator 35, the R-wave peak detection can be not triggered.

For another example, the first comparator 32 can compare a minimum value with a lower threshold value in the first register 31. If the minimum value is smaller than the lower threshold, the first comparator 32 can send a fourth logic signal 1 to the AND gate 36. The first comparator 32 can also provide a fifth logic signal for the second register 33. Based on the fifth logic signal, the second register 33 can send the stored first count associated with the time corresponding to the maximum value to the second comparator 35. The second register 33 can further store a second count from the first counter 34, in which the second count can be associated with a time corresponding to the minimum value. The first counter 34 can send the time corresponding to the minimum value to the second comparator 35. The second comparator 35 can determine a difference between the time corresponding to the maximum value and the time corresponding to the minimum value, and then further compare the difference with the predetermined R-wave time width. When the second comparator 35 determines that the difference is smaller than the predetermined R-wave time width, it can end a sixth logic signal 1 to the AND gate 36. When the AND gate 36 receives the fourth logic signal 1 from the first comparator 32 and the sixth logic signal 1 from the second comparator 35, the R-wave peak detection can be triggered.

In an implementation, the P wave and the T wave in the original ECG signal can be extracted based on the R-wave peak position, and the time-domain feature data described at the operation 408 can be obtained.

Due to ECG signal fluctuation, baseline drift and other factors, amplitude values for QRS waves at different times can be different, which can cause maximum values and minimum values to be different on different scales at the same time or on the same scale at different times. In this disclosure, a dynamic method can be used to determine extremum value thresholds used in the time-domain feature data, and accuracy of extracting the time-domain feature data can be improved by using dynamic extremum value thresholds. In FIG. 4D, as an example, a value in a third register 38 can be predetermined to be zero. A third comparator 37 can compare wavelet coefficients h at different scales with respective values stored in the third register 38. If the third comparator 37 finds a relatively large wavelet coefficient after the comparison, a logic control signal can be sent to the third register 38. In an example, the third register 38 can determine extremum value thresholds using the following method:

Upper threshold: MAX==p (a*max1+b*max2).
Lower threshold: MIN==q (a*min1+b*min2).

In the above equations, max1 is the maximum value of the wavelet coefficients detected in a first threshold detection cycle; min1 is the minimum value of the wavelet coefficients detected in the first threshold detection cycle; max2 is the maximum value of the wavelet coefficients detected in a second threshold detection cycle; and min2 is the minimum value of the wavelet coefficients detected in the second threshold detection cycle. a+b=1, in which a and b denote weights corresponding to the first threshold detection cycle and the second threshold detection cycle, respectively. p and q are positive numbers smaller than 1.

The extremum value thresholds calculated based on the method described above can be stored in the first register 31. A second counter 39 can control a current count. When the current count reaches a threshold detection cycle, the second counter 39 can clear the extremum value thresholds in the first register 31, so that the extremum value thresholds can be recalculated and updated at a next threshold detection cycle.

In this implementation, the time-domain feature data detection can be realized by hardware (e.g., registers and comparators), in which the time-domain feature data detection can become more real time. By using dynamic extremum value thresholds, accuracy of the time-domain feature data can be improved. By detecting P waves and T waves using detection results of R waves, detection speed can be improved and detection error rate can be reduced.

Figure 5:
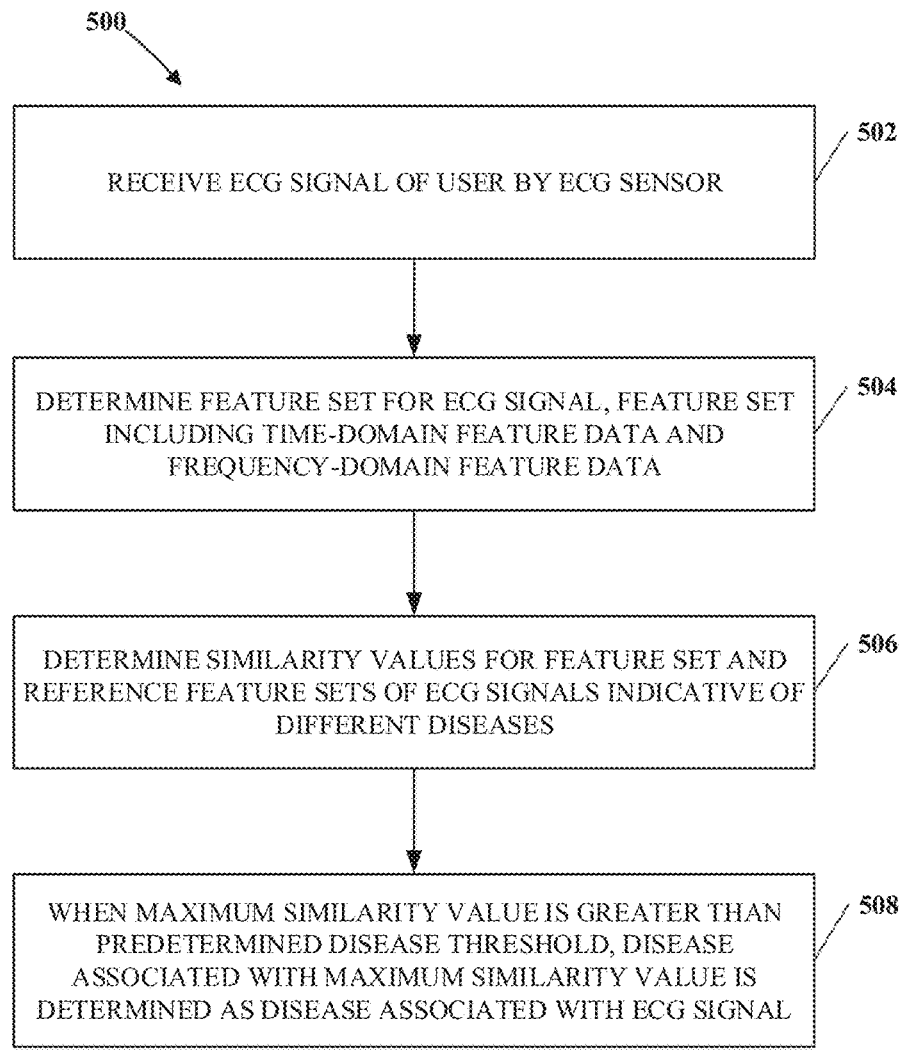
FIG. 5 is a flowchart of an example process for determining a disease based on a wearable device according to an implementation of this disclosure.

FIG. 5 is a flowchart of an example process 500 for determining a disease based on a wearable device according to an implementation of this disclosure. As shown in FIG. 5, the process 500 can include the following operations.

At operation 502, an original ECG signal of a user is received by an ECG sensor.

At operation 504, a feature vector (e.g., a feature vector) of the original ECG signal is determined. The feature vector can include time-domain feature data of the original ECG signal and frequency-domain feature data of the original ECG signal.

At operation 506, similarity values are determined between the feature vector of the original ECG signal and reference feature vectors of disease ECG signals that are indicative of different diseases.

At operation 508, when a maximum similarity value of the similarity values is greater than a first predetermined threshold (referred to as a "disease threshold"), a disease (e.g., a disease type) associated with the maximum similarity value is determined as a disease (e.g., a disease type) associated with the original ECG signal.

At the operation 506, for example, based on a feature vector (e.g., an eigenvector) of the original ECG signal ($\vec{x}$) the similarity values can be determined by the following formula:

$$d(\vec{x}, \vec{x}_r) = (\vec{x} - \vec{x}_r)^T M (\vec{x} - \vec{x}_r)$$

wherein $\vec{x}$ is the feature vector of the original ECG signal of the user. $\vec{x}_r$ is a feature vector of a disease ECG signal indicative of an r-th recorded disease, in which r is a positive integer. M is a matrix model that can be obtained using a machine learning technique, and elements of the matrix model can represent weight coefficients associated with the feature vector. T represents a transpose of the feature vector.

For example, when the wearable device is a smart wristband, the smart wristband can store reference feature vectors $\vec{x}_1$ and $\vec{x}_2$ associated with disease 1 and disease 2, respectively. The reference feature vectors $\vec{x}_1$ and $\vec{x}_2$ can be obtained by offline training using ECG signals of the disease 1 and the disease 2 recorded in medical case database management systems provided by relevant medical institutes. In an implementation, similarity values $d_1$ and $d_2$ can be calculated between the feature vector $\vec{x}$ and the reference feature vectors $\vec{x}_1$ and $\vec{x}^2$, respectively. A larger value of $d_1$ and $d_2$ can be determined. If the larger value of $d_1$ and $d_2$ is larger than the predetermined disease threshold, a disease type associated with the larger value can be determined as the disease type identified by the smart wristband. For example, if $d_1$ is greater than $d_2$ and further greater than the predetermined disease threshold, it can be determined that the user may have a disease associated with the reference feature vector $\vec{x}_1$. The predetermined disease threshold can be obtained by trial tests.

In an implementation, a latest case report can also be generated for the user based on the currently detected disease type for the user's reference.

In an implementation, if the maximum similarity value is smaller than the predetermined disease threshold, it can mean that the ECG signal detected by the ECG sensor is a normal ECG signal (e.g., indicative of the user having no cardiovascular disease), and a report can be generated for the user's reference.

In another implementation, to prevent private data of an authorized user breached by an unauthorized user stealing the smart wristband, identity information of the authorized user can be authenticated by the feature vector corresponding to the original ECG signal. After the authentication, disease detection can be performed to the ECG signal of the user at the operations 506 and 508.

Figure 6:
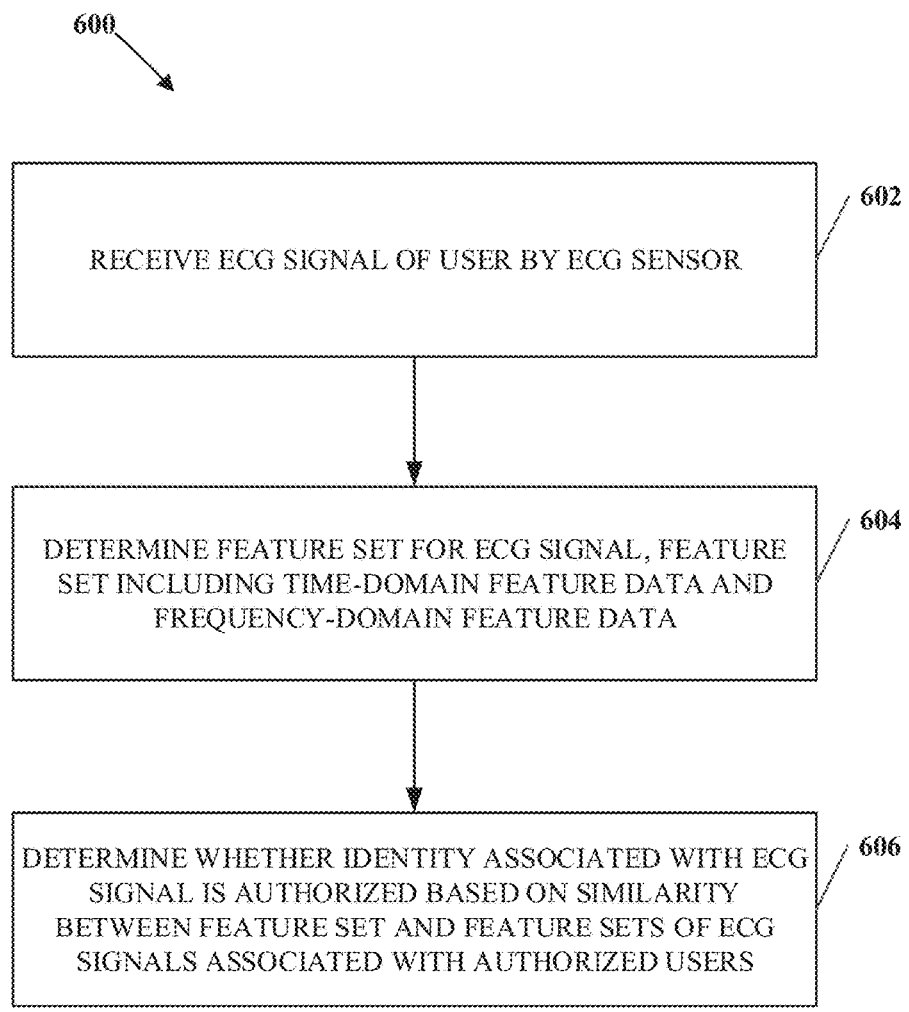
FIG. 6 is a flowchart of an example process for determining an identity based on a wearable device according to an implementation of this disclosure.

Referring to FIG. 6, an example process 600 for user identity authentication using the feature vector of the original ECG signal can include the following operations.

At operation 602, an original ECG signal of a user is received by an ECG sensor.

At operation 604, a feature vector (e.g., a feature vector) of the original ECG signal is determined. The feature vector can include time-domain feature data of the original ECG signal and frequency-domain feature data of the original ECG signal.

At operation 606, whether a user identity associated with the original ECG signal is authorized is determined based on similarity between the feature vector and reference feature vectors associated with ECG signals indicative of authorized users (referred to as "identity ECG signals").

At the operation 606, in an implementation, similarity values can be determined between the feature vector of an ECG signal of a current user and the reference feature vectors associated with the identity ECG signals indicative of the authorized users. When a maximum similarity value of the similarity values is greater than a second predetermined threshold (referred to as a "identity threshold"), the current user can be authenticated as authorized.

Figure 7:
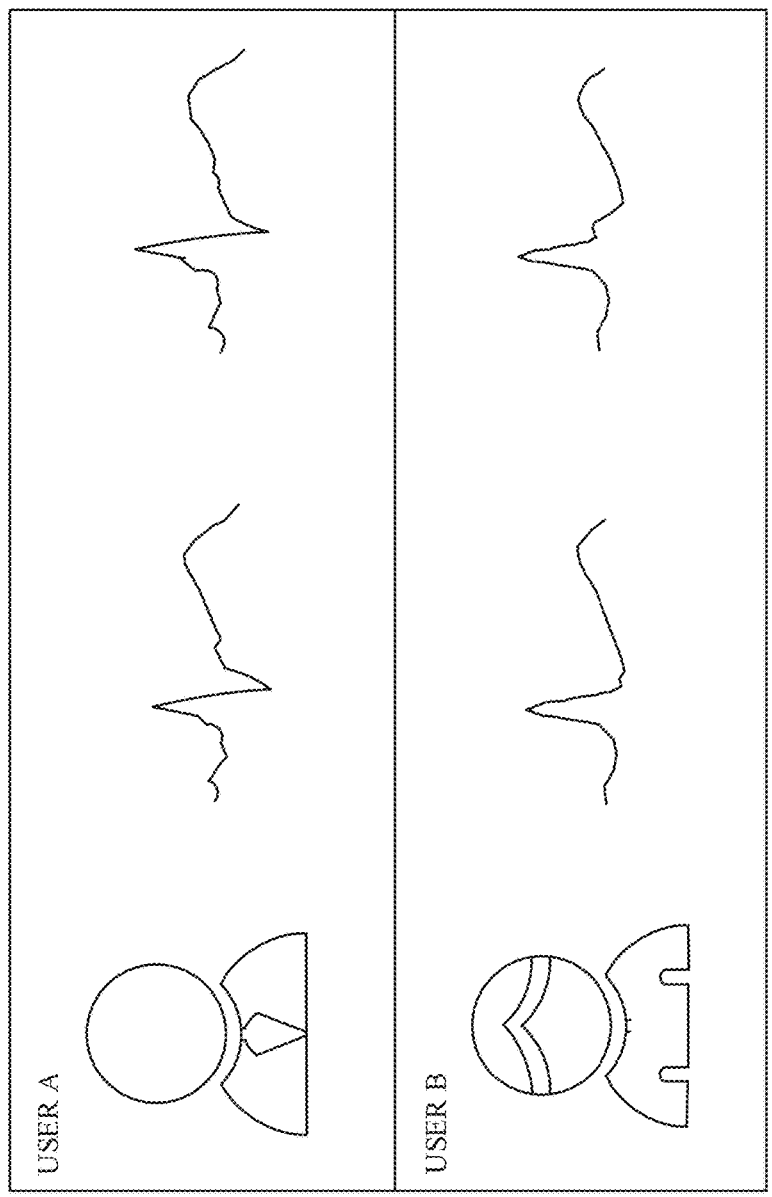
FIG. 7 is a diagram of example ECG signals of two different users.

For example, when the wearable device is a smart wristband, the smart wristband can store reference feature vectors $\vec{x}_A$ and $\vec{x}_b$ associated with user A and user B, respectively. As shown in FIG. 7, user A and user B have different shapes of ECG signals in time domain, therefore, they would also have different reference feature vectors, respectively. In an implementation, similarity values $d_A$ and $d_B$ can be calculated between the feature vector x of the ECG signal of the current user and the reference feature vectors $\vec{x}_A$ and $\vec{x}_B$, respectively. For example, if $d_A$ is greater than $d_B$ and further greater than the predetermined identity threshold, it can be determined that the current user of the smart wristband is user A.

In an implementation, a same user can be associated with multiple reference feature vectors. The multiple reference feature vectors can include reference feature vectors of the user at motion and reference feature vectors of the user at rest, respectively. For example, similarity values between the feature vector of the ECG signal of the current user and the multiple reference feature vectors associated with the same user can be determined, and a state of the user (e.g., a motion state or a static state) can be determined by a maximum similarity value of the similarity values.

It should be understood by persons skilled in the art that relevant parameters used in the similarity determination techniques for performing the disease detection and the identity authentication can be different or the same.

Implementations of this disclosure can perform disease detection or identity authentication using hardware, which can effectively shorten time for the detection and analysis. In addition, a matrix model obtained using a machine learning technique can increase correction rate of ECG recognition, which can further increase the accuracy of the disease detection.

Figure 8:
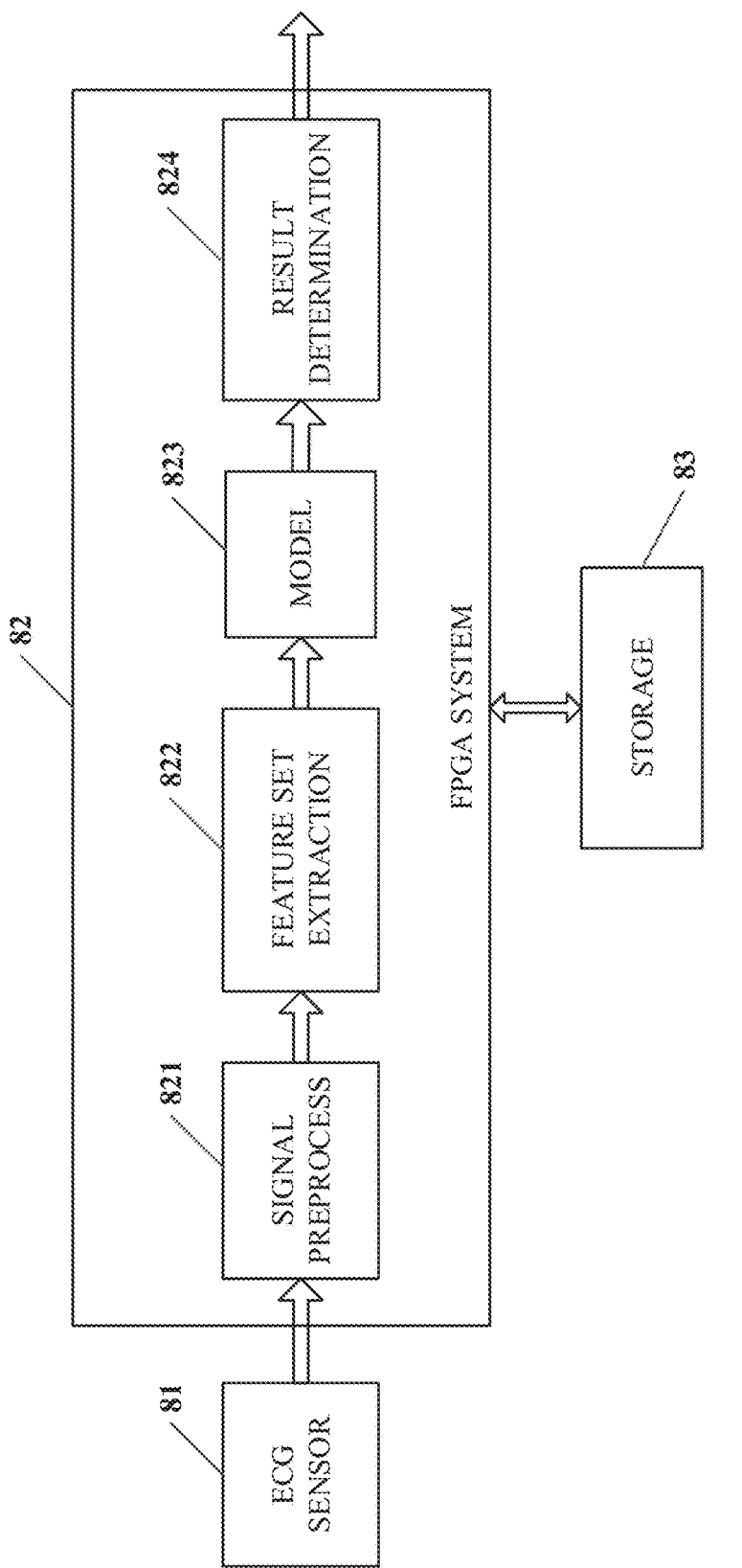
FIG. 8 is a diagram of an example structure of a wearable device according to an implementation of this disclosure.

FIG. 8 is a diagram of an example structure of a wearable device according to an implementation of this disclosure. In FIG. 8: an ECG sensor 81 can receive an original ECG signal; a signal preprocess module 821 can perform a wavelet transform for the original ECG signal and filter the transformed ECG signal to obtain wavelet coefficients; a feature vector extraction module 822 can determine time-domain feature data and frequency-domain feature data from the original ECG signal; a model 823 (e.g., implemented as a software module or a hardware module) can be used to compute similarity between the feature vector of the original ECG signal and reference feature vectors indicative of the user-interested information (e.g., a reference feature vector associated with a stored disease ECG signal, and/or a reference feature vector associated with an ECG signal of an authorized user); and a result determination module 824 can determine a state of the user-interested information based on the computed similarity (e.g., a disease detection result for the user, or whether the user has an authorized identity). In an implementation, the signal preprocess module 821, the feature vector extraction module 822, the model 823, and the result determination module 824 can be included in an FPGA system 82. In another implementation, a storage module 83 can further store feature vectors associated with various user-interested information (e.g., reference feature vectors associated with disease ECG signals, and reference feature vectors associated with ECG signals of authorized users). By storing the feature vectors, computational complexity of the FPGA system 82 can be reduced, time for ECG signal recognition can be shortened, and efficiency for the disease detection and the identity authentication can be improved.

Figure 9:
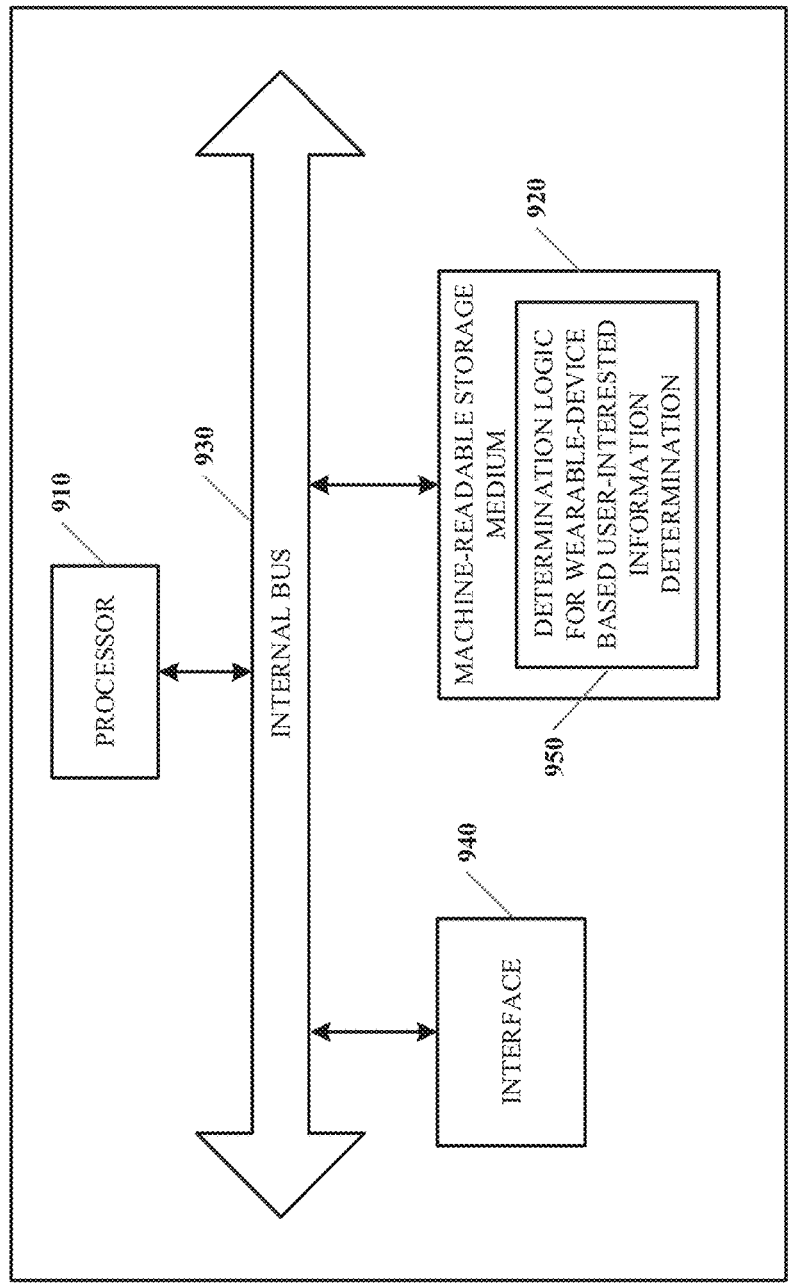
FIG. 9 is a diagram of an example hardware structure of an apparatus for determining user-interested information based on a wearable device according to an implementation of this disclosure.

This disclosure also provides an apparatus for determining user-interested information based on a wearable device. FIG. 9 shows a diagram of an example hardware structure of an apparatus for determining user-interested information based on a wearable device according to an implementation of this disclosure. In FIG. 9, the apparatus for determining user-interested information based on the wearable device can include a processor 910 and a machine-readable storage medium 920. The processor 910 and the machine-readable storage medium 920 can be connected by an internal bus 930. In other possible implementations, the apparatus can also include an external interface 940 for communication with other devices or components.

In various implementations, the machine-readable storage medium 920 can include a non-transitory memory, such as a random access memory (RAM), a flash memory or similar storage medium, or a combination thereof.

Figure 10:
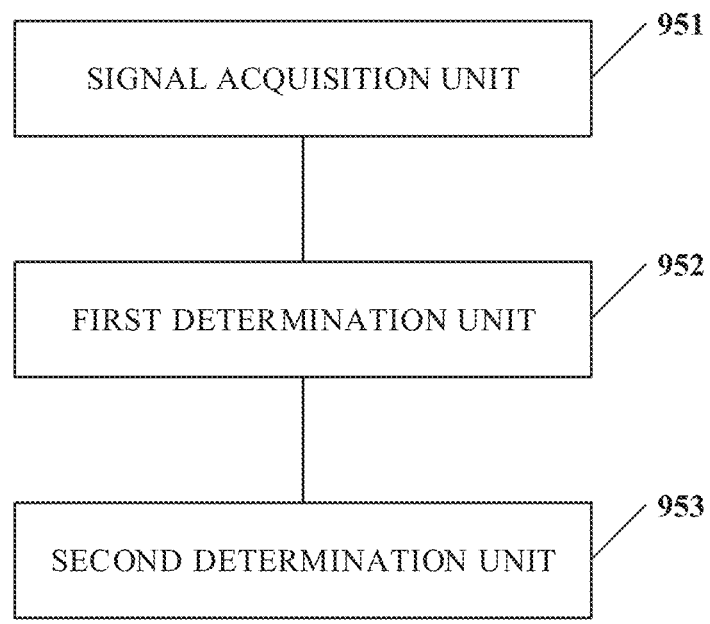
FIG. 10 is a block diagram of an example functional logic module for determining user-interested information based on a wearable device according to an implementation of this disclosure.
Figure 11:
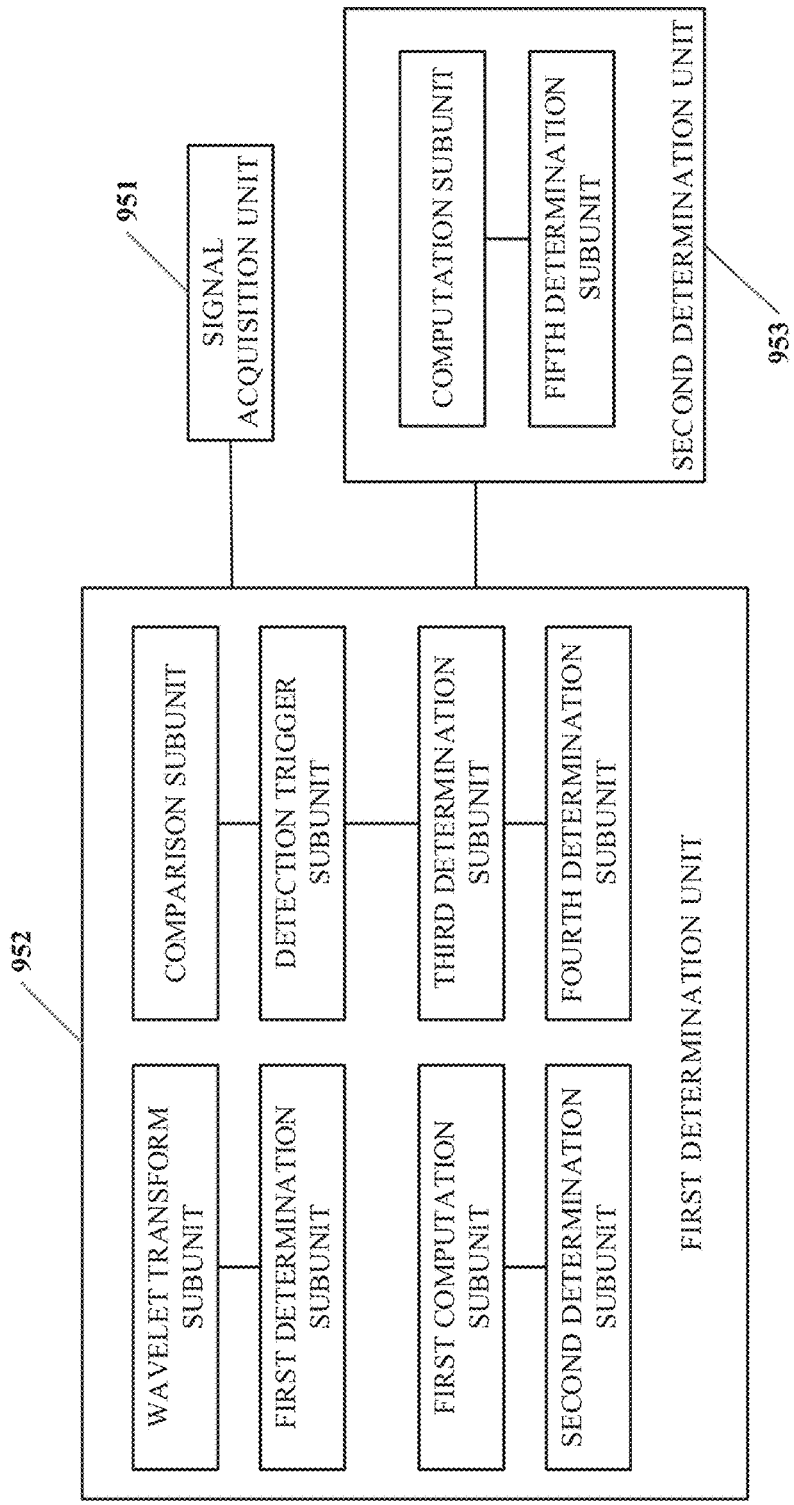
FIG. 11 is a block diagram of another example functional logic module for determining user-interested information based on a wearable device according to an implementation of this disclosure.

Further, as shown in FIG. 9, the machine-readable storage medium 920 can store machine-executable instructions corresponding to a determination logic 950 for wearable-device based user-interested information determination. Based on functions, the determination logic 950 can include a signal acquisition unit 951, a first determination unit 952, and a second determination unit 953, which are shown in FIG. 10.

The signal acquisition unit 951 is configured to receive an original ECG signal of a user through an ECG sensor integrated with the wearable device.

The first determination unit 952 is configured to determine a feature vector (e.g., a feature vector) of the original ECG signal. The feature vector can include time-domain feature data of the original ECG signal and frequency-domain feature data of the original ECG signal.

The second determination unit 953 is configured to determine the user-interested information based on similarity between the feature vector and reference feature vectors indicative of the user-interested information.

For example, the user-interested information can include health information. The second determination unit 953 can determine a disease (e.g., a disease type) associated with the original ECG signal based on the similarity between the feature vector of the original ECG signal and a reference feature vector associated with a disease ECG signal indicative of a disease.

For another example, the user-interested information can include identity information. The second determination unit 953 can determine whether a user identity associated with the ECG signal is authorized based on similarity between the feature vector and a reference feature vector associated with an identity ECG signal indicative of an authorized user.

In another implementation, the first determination unit 952 can include the following subunits. A wavelet transform subunit is configured to perform a wavelet transform to the original ECG signal to obtain wavelet coefficients of the original ECG signal. A first determination subunit is configured to determine the wavelet coefficients as first frequency-domain feature data of the original ECG signal.

In another implementation, the first determination unit 952 can further include the following subunits. A first computation subunit is configured to perform an AC operation and a DCT to the ECG signal after the wavelet transform and filtered, to obtain DCT coefficients after the AC and DCT. A second determination subunit is configured to determine the DCT coefficients as second frequency-domain feature data of the original ECG signal.

In another implementation, the first determination unit 952 can further include the following subunits.

A comparison subunit is configured to compare extremum values of the wavelet coefficients with corresponding extremum thresholds.

A detection subunit is configured to trigger R-wave peak detection when two consecutive extremum values are within their respective extremum thresholds and a time difference between the two extremum values is smaller than a predetermined R-wave time width.

A third determination subunit is configured to extract a P wave and a T wave from the original ECG signal based on a position of the R-wave peak.

A fourth determination subunit is configured to determine the time-domain feature data for the original ECG signal based on the R-wave peak position, the P wave, and the T wave. The time-domain feature data can include: the position of the R-wave peak, a peak position of the P wave, a peak position of the T wave, an amplitude of the P wave, an amplitude of the R wave, an amplitude of the T wave, a difference between the peak position of the P wave and the position of the R-wave peak, a difference between the peak position of the T wave and the position of the R-wave peak, a PR segment, and an ST segment.

In another implementation, the second determination unit 953 can include the following subunits.

A computation subunit is configured to compute similarity values between the feature vector of the original ECG signal and the reference feature vectors indicative of the user-interested information.

A fifth determination subunit is configured to determine the user-interested information associated with a maximum similarity value of the similarity values as the user-interested information associated with the original ECG signal when the maximum similarity value is greater than a predetermined user-interested threshold.

In an example, the similarity value can be computed using the following formula:

$$d(\vec{x}, \vec{x}_r) = (\vec{x} - \vec{x}_r)^T M(\vec{x} - \vec{x}_r)$$

wherein $\vec{x}$ is the feature vector of the original ECG signal of the user. $\vec{x}_r$ is a feature vector of a disease ECG signal indicative of an r-th recorded disease, in which r is a positive integer. M is a matrix model that can be obtained using a machine learning technique, and elements of the matrix model can represent weight coefficients associated with the feature vector.

As an example, the determination logic 950 can be implemented as software. An example process of how a wearable device can execute the determination logic 950 is described as follows. In this example, the determination logic 950 for wearable device-based user-interested information determination can include a set of computer-executable instructions stored in the machine-readable storage medium 920. When a processor 910 in a wearable device executes the logic 950, the processor 910 can invoke the instructions associated with the determination logic 950 stored in the machine-readable storage medium 920 to perform the following operations.

An original ECG signal of a user is received by an ECG sensor integrated in the wearable device. A feature vector of the original ECG signal is determined. The feature vector can include time-domain feature data of the original ECG signal and frequency-domain feature data of the original ECG signal. The user-interested information is determined based on similarity between the feature vector of the original ECG signal and reference feature vectors indicative of the user-interested information.

In an implementation, the user-interested information can include health information. When the user-interested information is being determined based on the similarity between the feature vector and the reference feature vectors indicative of the user-interested information, the computer-executable instructions can cause the processor to determine a disease type associated with the original ECG signal based on similarity between the feature vector of the original ECG signal and a reference feature vector of a disease ECG signal.

In another implementation, the user-interested information can include identity information. When the user-interested information is being determined based on the similarity between the feature vector and the reference feature vectors indicative of the user-interested information, the computer-executable instructions can cause the processor to determine whether a user identity associated with the original ECG signal is authorized based on similarity between the feature vector of the original ECG signal and a reference feature vector of an ECG signal of an authorized user.

In an implementation, when determining the feature vector of the original ECG signal, computer-executable instructions can cause the processor to: perform a wavelet transform to the original ECG signal to obtain wavelet coefficients of the original ECG signal; and determine the wavelet coefficients as first frequency-domain feature data of the original ECG signal.

In an implementation, when determining the feature vector of the original ECG signal, the computer-executable instructions can cause the processor to: perform an AC operation and a DCT on the ECG signal after the wavelet transform and filtered, to obtain DCT coefficients after the AC and DCT; and determine the DCT coefficients as second frequency-domain feature data of the original ECG signal.

In another implementation, when determining a feature vector of the original ECG signal, the computer-executable instructions can cause the processor to: compare (e.g., by a comparator) extremum values of the wavelet coefficients with corresponding extremum thresholds; trigger detection of the R-wave peak when two consecutive extremum values are within their respective extremum thresholds and a time difference between the two extremum values is smaller than a predetermined R-wave time width; extract a P wave and a T wave of the ECG signal based on a position of the R-wave peak; and determine the time-domain feature data of the ECG signal from at least one of the R-wave peak, the P wave, and the T wave. The time-domain feature data of the ECG signal can include at least one of: the peak position of the R wave, a peak position of the P wave, a peak position of the T wave, an amplitude of the P wave, an amplitude of the R wave, an amplitude of the T wave, a difference between the peak position of the P wave and the peak position of the R wave, a difference between the peak position of the T wave and the position of the peak position of the R wave, a PR segment, and an ST segment.

In another implementation, when the user-interested information is being determined based on the similarity between the feature vector and the reference feature vectors indicative of the user-interested information, the computer-executable instructions can cause the processor to calculate similarity values between the feature vector of the original ECG signal and the reference feature vectors representing the user-interested information; and, when a maximum similarity value of the similarity values is greater than a predetermined threshold, determine the user-interested information associated with the maximum similarity value as the user-interested information associated with the original ECG signal.

In an example, the similarity value can be computed using the following formula:

$$d(\vec{x}, \vec{x}_r) = (\vec{x} - \vec{x}_r)^T M (\vec{x} - \vec{x}_r)$$

wherein $\vec{x}$ is the feature vector of the original ECG signal of the user. $\vec{x}_r$ is a feature vector of a disease ECG signal indicative of an r-th recorded disease, in which r is a positive integer. M is a matrix model that can be obtained using a machine learning technique, and elements of the matrix model can represent weight coefficients associated with the feature vector.

As described above, it should be noted that all or a portion of aspects of the disclosure described herein can be implemented using a general purpose computer/processor with a computer program that, when executed, carries out any of the respective techniques, algorithms and/or instructions described herein. In addition, or alternatively, for example, a special purpose computer/processor can be utilized which can contain specialized hardware for carrying out any of the techniques, algorithms, or instructions described herein.

The implementations of computing devices as described herein (and the algorithms, methods, instructions, etc., stored thereon and/or executed thereby) can be realized in hardware, software, or any combination thereof. The hardware can include a field-programmable gate array (FPGA). In the claims, the term "processor" should be understood as encompassing any of the foregoing, either singly or in combination. The terms "signal" and "data" are used interchangeably. Further, portions of the computing devices do not necessarily have to be implemented in the same manner.

The aspects herein can be described in terms of functional block components and various processing operations. The disclosed processes and sequences may be performed alone or in any combination. Functional blocks can be realized by any number of hardware and/or software components that perform the specified functions. For example, the described aspects can employ various integrated circuit components, e.g., memory elements, processing elements, logic elements, look-up tables, and the like, which can carry out a variety of functions under the control of one or more microprocessors or other control devices. Functional aspects can be implemented in algorithms that execute on one or more processors.

Implementations or portions of implementations of the above disclosure can take the form of a computer program product accessible from, for example, a computer-usable or computer-readable medium. A computer-usable or computer-readable medium can be any device that can, for example, tangibly contain, store, communicate, or transport a program or data structure for use by or in connection with any processor. The medium can be, for example, an electronic, magnetic, optical, electromagnetic, or a semiconductor device. Other suitable mediums are also available. Such computer-usable or computer-readable media can be referred to as non-transitory memory or media, and can include RAM or other volatile memory or storage devices that can change over time. A memory of an apparatus described herein, unless otherwise specified, does not have to be physically contained by the apparatus, but is one that can be accessed remotely by the apparatus, and does not have to be contiguous with other memory that might be physically contained by the apparatus.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. In other words, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an aspect" or "one aspect" throughout is not intended to mean the same implementation or aspect unless described as such.

The use of "including" or "having" and variations thereof herein is meant to encompass the items listed thereafter and equivalents thereof as well as additional items. Unless specified or limited otherwise, the terms "mounted," "connected," 'supported," and "coupled" and variations thereof are used broadly and encompass both direct and indirect mountings, connections, supports, and couplings. Further, "connected" and "coupled" are not restricted to physical or mechanical connections or couplings.

The use of the terms "a" and "an" and "the" and similar referents in the context of describing the disclosure (especially in the context of the following claims) should be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein are performable in any suitable order unless otherwise indicated herein or otherwise clearly contradicted by context. The use of examples, or exemplary language (e.g., "such as") provided herein, is intended merely to better illuminate the disclosure and does not pose a limitation on the scope of the disclosure unless otherwise claimed.

While the disclosure has been described in connection with certain implementations and implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for determining a cardiovascular disease of a user using a wearable device, comprising:
   receiving, by an electrocardiography (ECG) sensor associated with the wearable device, an ECG signal of the user, the ECG signal corresponding a physical ECG signal of the user;
   determining a feature set for the ECG signal, wherein the feature set comprises time-domain feature data of the ECG signal and frequency-domain feature data of the ECG signal, the determining the feature set for the ECG signal comprising:
      determining wavelet coefficients for the ECG signal by performing a wavelet transform to the ECG signal;
      determining the wavelet coefficients as a first type of the frequency-domain feature data of the ECG signal;
      determining discrete cosine transform (DCT) coefficients by performing autocorrelation (AC) and DCT to the ECG signal filtered after the wavelet transform; and
      determining the DCT coefficients as a second type of the frequency-domain feature data of the ECG signal;
   determining whether the user has the cardiovascular disease based on a similarity between the feature set and reference feature sets of cardiovascular diseases; and
   on condition that the user is determined to have the cardiovascular disease, reporting to the user that the user has the cardiovascular disease.

2. The method of claim 1, wherein determining the cardiovascular disease of the user based on the similarity between the feature set and the reference feature sets of the cardiovascular diseases comprises:
   determining a disease type associated with the ECG signal based on similarity between the feature set and a first reference feature set associated with a first ECG signal indicative of a disease.

3. The method of claim 1, further comprising:
   determining whether a user identity associated with the ECG signal is authorized based on similarity between the feature set and a second reference feature set associated with a second ECG signal indicative of an authorized user.

4. The method of claim 1, wherein determining the feature set for the ECG signal comprises:
   determining, for extremum values of the wavelet coefficients comprising at least one of maximum values and minimum values, whether a first extremum value is within a first extremum value threshold and a second extremum value is within a second extremum value threshold;
   determining an R-wave peak of an R wave based on a determination that the first extremum value and the second extremum value are consecutive, the first extremum value is within the first extremum value threshold, the second extremum value is within the second extremum value threshold, and a time difference between the first extremum value and the second extremum value is smaller than a predetermined R-wave time width;
   determining a P wave and a T wave for the ECG signal based on a position of the R-wave peak; and
   determining the time-domain feature data of the ECG signal based on at least one of the R-wave peak, the P wave, and the T wave, wherein the time-domain feature data comprises at least one of: the position of the R-wave peak, a peak position of the P wave, a peak position of the T wave, an amplitude of the P wave, an amplitude of the R wave, an amplitude of the T wave, a difference between the peak position of the P wave and the position of the R-wave peak, a difference between the peak position of the T wave and the position of the R-wave peak, a PR segment, and an ST segment.

5. The method of claim 1, wherein determining whether the user has the cardiovascular disease based on the similarity between the feature set and the reference feature sets of the cardiovascular diseases comprises:
   determining similarity values for the feature set and the reference feature sets of the cardiovascular diseases, wherein a similarity value of the similarity values is determined between the feature set and a reference feature set of the reference feature sets; and
   based on a determination that a maximum similarity value of the similarity values is greater than a predetermined threshold and the maximum similarity value being associated with the cardiovascular disease, determining that the user has the cardiovascular disease.

6. The method of claim 5, wherein determining the similarity values for the feature set and the reference feature sets comprises:
- determining a difference set using the feature set and the reference feature set, wherein a record in the difference set is determined as a difference between a record in the feature set and a corresponding record in the reference feature set; and
- determining the similarity value for the feature set and the reference feature set using a weighted sum model comprising weights associated with records of the feature set, wherein the weights are determined using a machine learning technique, and the similarity value is determined as a weighted sum of records in the difference set using the weights.

7. The method of claim 1, further comprising:
on condition that the user is determined not to have the cardiovascular disease, reporting to the user that the user has a normal ECG signal.

8. The method of claim 1, further comprising:
on condition that the user is determined not to have the cardiovascular disease, reporting to the user that the user does not have the cardiovascular disease.

9. A wearable device for determining cardiovascular diseases of a user of the wearable device, comprising:
- an electrocardiography (ECG) sensor, configured to receive an ECG signal of the user;
- a field-programmable gate array (FPGA) system, configured to determine whether the user has a cardiovascular disease based on the ECG signal, further comprising:
  - a feature set determination module, configured to determine a feature set for the ECG signal, wherein the feature set comprises time-domain feature data of the ECG signal and frequency-domain feature data of the ECG signal;
  - a processing module, configured to determine wavelet coefficients by performing a wavelet transform and filtering to the ECG signal;
  - a model used to determine similarity values for the feature set and reference feature sets of cardiovascular diseases; and
  - a result determination module, configured to determine whether the user has the cardiovascular disease based on the similarity values; and
- a memory including instructions executable by a processor to:
  - report to the user whether the user has the cardiovascular disease.

10. An apparatus for determining cardiovascular information of a user based on a wearable device, comprising:
- a processor; and
- a memory coupled to the processor, the memory configured to store instructions which when executed by the processor become operational with the processor to:
  - receive, by an electrocardiography (ECG) sensor associated with the wearable device, an ECG signal of the user;
  - determine a feature set for the ECG signal, wherein the feature set comprises time-domain feature data of the ECG signal and frequency-domain feature data of the ECG signal by:
    - determining wavelet coefficients for the ECG signal by performing a wavelet transform to the ECG signal; and
    - determining the wavelet coefficients as a first type of the frequency-domain feature data of the ECG signal;
  - determine the cardiovascular information based on a similarity between the feature set and reference feature sets of cardiovascular diseases; and
  - report to the user the cardiovascular information.

11. The apparatus of claim 10, wherein the instructions operational with the processor to determine the cardiovascular information based on the similarity between the feature set and reference feature sets of cardiovascular diseases further comprise instructions to:
determine a disease type associated with the ECG signal based on similarity between the feature set and a first reference feature set associated with a first ECG signal indicative of a disease.

12. The apparatus of claim 10, wherein the instructions further comprise instructions to:
determine whether a user identity associated with the ECG signal is authorized based on similarity between the feature set and a second reference feature set associated with a second ECG signal indicative of an authorized user.

13. The apparatus of claim 10, wherein the instructions operational with the processor to determine the feature set for the ECG signal further comprise instructions to:
- determine discrete cosine transform (DCT) coefficients by performing autocorrelation (AC) and DCT to the ECG signal filtered after the wavelet transform; and
- determine the DCT coefficients as a second type of the frequency-domain feature data of the ECG signal.

14. The apparatus of claim 10, wherein the instructions operational with the processor to determine the feature set for the ECG signal further comprise instructions to:
- determine, for extremum values of the wavelet coefficients comprising at least one of maximum values and minimum values, whether a first extremum value is within a first extremum value threshold and a second extremum value is within a second extremum value threshold;
- determine an R-wave peak of an R wave based on a determination that the first extremum value and the second extremum value are consecutive, the first extremum value is within the first extremum value threshold, the second extremum value is within the second extremum value threshold, and a time difference between the first extremum value and the second extremum value is smaller than a predetermined R-wave time width;
- determine a P wave and a T wave for the ECG signal based on a position of the R-wave peak; and
- determining the time-domain feature data of the ECG signal based on at least one of the R-wave peak, the P wave, and the T wave, wherein the time-domain feature data comprises at least one of: the position of the R-wave peak, a peak position of the P wave, a peak position of the T wave, an amplitude of the P wave, an amplitude of the R wave, an amplitude of the T wave, a difference between the peak position of the P wave and the position of the R-wave peak, a difference between the peak position of the T wave and the position of the R-wave peak, a PR segment, and an ST segment.

15. The apparatus of claim 10, wherein the instructions operational with the processor to determine the cardiovascular information based on the similarity between the feature set and the reference feature sets of the cardiovascular diseases further comprise instructions to:
determine similarity values for the feature set and the reference feature sets of the cardiovascular diseases, wherein a similarity value of the similarity values is determined between the feature set and a reference feature set of the reference feature sets; and based on a determination that a maximum similarity value of the similarity values is greater than a predetermined threshold, determine the cardiovascular information as being the cardiovascular information associated with the maximum similarity value.

16. The apparatus of claim 15, wherein the instructions operational with the processor to determine the similarity values for the feature set and the reference feature sets further comprise instructions to:

determine a difference set using the feature set and the reference feature set, wherein a record of a data type in the difference set is determined as a difference between a first record of the data type in the feature set and a second record of the data type in the reference feature set; and determine the similarity value for the feature set and the reference feature set using a weighted sum model comprising weights associated with records of the feature set, wherein the weights are determined using a machine learning technique, and the similarity value is determined as a weighted sum of records in the difference set using the weights.

* * * * *